US010394009B2

(12) United States Patent
Rogers et al.

(10) Patent No.: US 10,394,009 B2
(45) Date of Patent: Aug. 27, 2019

(54) POLARISATION MICROSCOPE

(71) Applicant: University of Southampton, Southampton (GB)

(72) Inventors: Edward Thomas Foss Rogers, Ashurst (GB); Peter John Shand Smith, Lockerley (GB)

(73) Assignee: University of Southampton, Hampshire (GB)

( * ) Notice: Subject to any disclaimer, the term of this patent is extended or adjusted under 35 U.S.C. 154(b) by 0 days.

(21) Appl. No.: 15/758,546

(22) PCT Filed: Sep. 7, 2016

(86) PCT No.: PCT/GB2016/052763
§ 371 (c)(1),
(2) Date: Mar. 8, 2018

(87) PCT Pub. No.: WO2017/042556
PCT Pub. Date: Mar. 16, 2017

(65) Prior Publication Data
US 2018/0246307 A1 Aug. 30, 2018

(30) Foreign Application Priority Data
Sep. 8, 2015 (GB) .................................. 1515862.9

(51) Int. Cl.
*G01N 21/21* (2006.01)
*G02B 21/00* (2006.01)
*G02B 27/58* (2006.01)

(52) U.S. Cl.
CPC ......... *G02B 21/0068* (2013.01); *G01N 21/21* (2013.01); *G02B 21/0032* (2013.01);
(Continued)

(58) Field of Classification Search
CPC ........... G01N 21/21; G01N 2201/0675; G02B 21/0024; G02B 21/0028; G02B 21/0032;
(Continued)

(56) References Cited

U.S. PATENT DOCUMENTS 5,521,705 A 5/1996 Oldenbourg et al.
6,856,391 B2 2/2005 Garab et al.
(Continued)

FOREIGN PATENT DOCUMENTS

CN 101 852 594 B 5/2012

OTHER PUBLICATIONS

International Search Report and Written Opinion for corresponding Patent Application No. PCT/GB2016/052763 dated Nov. 11, 2016.
(Continued)

*Primary Examiner* — Gordon J Stock, Jr.
(74) *Attorney, Agent, or Firm* — Renner, Otto, Boisselle & Sklar, LLP

(57) ABSTRACT

A super-resolution scanning confocal polarization contrast microscope is provided. The microscope has a laser light source (1), sample stage (10) for mounting a sample 6 and detector (8). A polarization controller (3) is used to set the polarization state of the light beam to any one of a defined set of different polarization states. A spatial light modulator (5) modulates the light beam in amplitude and/or phase to focus a sub-diffraction-limit central spot on the sample together with unwanted sidebands. A scanning confocal scheme is used with a pin hole 9 in front of the detector (8) so that only that portion of the light is detected which has come from the central spot, while rejecting light that has been scattered by the sample from the sidebands. Polarization contrast images with sub-diffraction limit resolution can thus be acquired.

16 Claims, 3 Drawing Sheets

(52) U.S. Cl.
CPC .. *G01N 2201/0675* (2013.01); *G02B 21/0072* (2013.01); *G02B 21/0092* (2013.01); *G02B 27/58* (2013.01)

(58) Field of Classification Search
CPC ............. G02B 21/0036; G02B 21/004; G02B 21/0048; G02B 21/0068; G02B 21/0072; G02B 21/0076; G02B 21/0092; G02B 27/58
See application file for complete search history.

(56) References Cited

U.S. PATENT DOCUMENTS

| | | | | |
|---|---|---|---|---|
| 6,924,893 | B2* | 8/2005 | Oldenbourg | G02B 21/0004 356/369 |
| 7,202,950 | B2 | 4/2007 | Shribak et al. | |
| 8,896,683 | B2* | 11/2014 | Borovytsky | G02B 21/06 348/79 |
| 9,007,451 | B2* | 4/2015 | Rogers | G02B 21/0084 348/79 |
| 9,507,135 | B2* | 11/2016 | Iketaki | G02B 21/0032 |
| 9,568,741 | B2* | 2/2017 | Dholakia | G02B 27/58 |
| 10,151,634 | B2* | 12/2018 | Abdulhalim | G02B 27/286 |
| 10,156,669 | B2* | 12/2018 | Beresna | G02B 5/1809 |
| 10,191,268 | B2* | 1/2019 | Leger | G02B 21/0036 |
| 2010/0214404 | A1* | 8/2010 | Chen | G02B 21/0032 348/79 |
| 2011/0140000 | A1* | 6/2011 | Iketaki | G02B 21/0068 250/458.1 |
| 2013/0235180 | A1 | 9/2013 | Rogers et al. | |
| 2015/0211986 | A1 | 7/2015 | Kuang et al. | |
| 2017/0038574 | A1* | 2/2017 | Zhuang | G02B 21/0068 |
| 2017/0336326 | A1* | 11/2017 | Sirat | G02B 21/0056 |

OTHER PUBLICATIONS

Rudolf Oldenbourg; "Polarization microscopy with the LC-PolScope", Marine Biological Laboratory, Nov. 2003, pp. 1-42.
Jörg Baumgartl et al., "Far field subwavelength focusing using optical eigenmodes", American Institue of Physics, Appl. Phys. Lett. 98, 181109 (2011).
M. Mazilu et al., "Optical Eigenmodes; exploiting the quadratic nature of the energy flux and of scattering interactions", Optics Express, pp. 933-945, vol. 19, No. 2, Jan. 17, 2011.
Shalin B. Mehta et al., "Polarized light imaging of birefringence and diattenuation at high resolution and high sensitivity", Journal of Optics 15 (2013), pp. 1-13.
Curt McKenna et al., "Maskless Direct Write Grayscale Lithography for MEMS Applications", Dept. of Electrical and Computer Engineering, University of Louisville, Louisville, KY, USA, 2010.
C.M. Waits et al., "Microfabrication of 3D silicon MEMS structures using gray-scale lithography and deep reactive ion etching", Sensors and Actuators A 119 (2005), pp. 245-253.
Q. Wang et al., "1.7 Gbit/in.2 gray-scale continuous-phase-change femtosecond image storage", Applied Physics Letters 104, 121105 (2014).

* cited by examiner

POLARISATION MICROSCOPE

This application is a national phase of International Application No. PCT/GB2016/052763 filed Sep. 7, 2016 and published in the English language, which claims priority to United Kingdom Patent Application No. 1515862.9 filed Sep. 8, 2015, which are hereby incorporated herein by reference.

BACKGROUND OF THE INVENTION

The invention relates to a polarisation microscope.

Polarisation microscopy is a technique which uses polarised light to illuminate a sample in order to probe polarisation anisotropy in the sample, which is then used as the contrast mechanism for imaging.

Light may be polarised linearly, i.e. in a single direction, or so that the polarisation state rotates to form circularly or elliptically polarised light. For rotating polarisation, the rotation may be clockwise or anti-clockwise so that the rotation has chirality or handedness. Polarisation microscopy will most commonly look at differences in how rotating polarisation components of opposite handedness propagate through or are reflected from a sample.

The physical properties probed by polarisation anisotropy include: birefringence, luminescence (including fluorescence as used in biological sciences); and diattenuation (sometimes called dichroism, although this latter term can have other meanings).

The development of polarisation microscopy in recent decades owes a great deal to work initiated by Rudolf Oldenbourg at the Marine Biological Laboratory (MBL) in Woods Hole, Mass., USA. The trade name used by this group for microscopes following their design is "PolScope" or "LC-PolScope", where LC refers to liquid crystal and in particular use of a pair of liquid crystal retarder plates in a so-called universal compensator in which each retarder functions as a linear retarder having a retardance amount which can be adjusted by varying an applied voltage.

The original US patent from the Oldenbourg group is U.S. Pat. No. 5,521,705 [ref. 1] which was filed in 1994 and published in 1996. A later patent is U.S. Pat. No. 7,202,950 [ref. 2] filed in 2003 and published in 2007 describes a development of the original technique which applies a defined set of four or five polarisation states to determine retardance more accurately. A relatively up-to-date description of the polarisation microscope developed from this work is the November 2003 review article: "Polarization microscopy with the LC-PolScope" [ref. 3] which is available online as a pdf document. An abridged version was published in: R. D. Goldman and D. L. Spector, editors. Live Cell Imaging: A Laboratory Manual. Cold Spring Harbor, N.Y.: Cold Spring Harbor Laboratory Press. p 205-37.

The "PolScope" microscope was sold under the trade mark "SpindleView" and is now sold under the trade mark "Oosight". Originally the microscope was sold by Cambridge Research & Instrumentation (CRi), which was later acquired by Caliper Life Sciences in 2010, which in turn was acquired by Perkin Elmer in 2011. Recently, in 2015, Perkin Elmer sold the PolScope microscope business to Hamilton Thorne. Information and user support is also done in parallel through the "OpenPolScope" organisation also set up by MBL.

A scanning confocal microscope which incorporates polarisation contrast is also known from U.S. Pat. No. 6,856,391 [ref. 4], with a 2000 priority date, which originates from the Biological Research Centre in Szeged, Hungary and is licensed to Zeiss.

SUMMARY OF THE INVENTION

According to one aspect of the invention there is provided a microscope comprising:
  a light source operable to generate a light beam of a particular wavelength;
  a sample stage configured to position a relevant portion of a sample in a sample position at a focus of the light beam;
  a detector arranged to collect light from the sample position to collect a sample image for display;
  a polarisation controller arranged in the light beam either before or after the sample position and operable to set the polarisation state of the light beam to any one of a defined set of different polarisation states;
  a spatial light modulator arranged to receive the light beam from the light source before the sample position, the spatial light modulator being configured to spatially modulate the light beam in amplitude and/or phase so that it focuses the light beam at the sample position in a focal plane with an intensity profile having a central peak with a full width half maximum of less than half the wavelength and sideband peaks; and
  a pin hole arranged to permit only that portion of the light beam to be detected by the detector which has comes from the central peak, while rejecting portions of the light beam that have been scattered by the sample from the sideband peaks.

This microscope is a type of scanning confocal polarisation microscope which can be implemented to acquire, at high speed, super-resolution polarisation contrast images.

The polarisation controller may comprise first and second variable light retarders each of which is independently controlled to set the polarisation state to one of the defined set of different polarisation states.

In some embodiments, the spatial light modulator (SLM) is programmable (i.e. reconfigurable) to provide a predefined spatial modulation of the light beam in amplitude and/or phase. In other embodiments, the spatial light modulator is a fixed (i.e. not programmable) mask whose structure (i.e. physical properties) spatially modulates the light beam in amplitude and/or phase. Such a fixed mask may be formed from a binary mask which is generally opaque but is structured with a pattern of optically transparent apertures to spatially modulate the light beam in amplitude. The fixed mask may alternatively be configured to cause variable amplitude and phase transmission, thereby to spatially modulate the beam in amplitude and phase. Such an amplitude-and-phase modulating fixed mask may be formed from a glass plate of variable thickness with a variable partially absorbing or reflecting layer deposited on it. Such masks may be fabricated, for example, using greyscale lithography [refs. 9, 10] or by direct laser writing into a suitable medium [ref.11]. Additionally, a combination of a programmable SLM, such as a liquid crystal (LC) panel, and a fixed binary or variable transmission mask may be used.

A beam scanner can be provided to scan the beam over the sample. The beam scanner is arranged before the sample position to scan the light beam laterally over the sample position. Instead of a beam scanner, or as well as a beam scanner, the sample stage can be provided with positioning elements which allow it to scan the sample position laterally across the light beam. These two options are functionally the same.

The detector and pin hole can be arranged to collect light transmitted through the sample position in transmission mode or to collect light reflected from the sample position in reflection mode. In transmission mode, an imaging lens is provided to relay light from the sample to the detector. In reflection mode, a common lens can be used both for focusing the light onto the sample and collecting the light reflected from the sample and relaying it to the detector. If desired, a single microscope can be provided with two sets of detection components, one for transmission and one for reflection, and these can be used singly or in combination as desired.

In most embodiments, the polarisation controller is provided in combination with a polarisation analyser, such that the polarisation controller is arranged before or after the sample position, and the polarisation analyser is arranged respectively after or before the sample position. The polarisation analyser may be a circular polariser. However, there is a group of embodiments which dispenses with a polarisation analyser, namely when the images measure variations in reflectivity or absorption as a function of polarisation of the sample.

According to another aspect of the invention there is provided a confocal imaging method comprising:
(a) providing an object to be imaged;
(b) generating a light beam of a particular wavelength;
(c) configuring a polarisation controller to retard the light beam before or after the sample by an amount which sets the polarisation state of the light beam to one of a defined set of different polarisation states;
(d) spatially modulating the light beam in amplitude and/or phase to create a focused spot at the sample having an intensity profile in the focal plane with a full width half maximum of less than half the wavelength;
(e) traversing the focused spot across an area of the sample and for each spot position on the sample measuring the light intensity distribution across a conjugate image plane where a detector is positioned in order to build up an image specific to the current polarisation state;
(f) repeating the steps (c), (d) and (e) for each of the other polarisation states to collect corresponding images and thereby completely to acquire said set of images; and
(g) combining said set of images into a single polarisation contrast image.

The polarisation contrast image can of course be stored in a storage device or displayed on a display device as desired using suitable data storage and display technology.

In one modality, the detector is arranged in reflection mode and the images measure variations in reflectivity as a function of polarisation of the sample—we refer to this modality as direflection. Image acquisition with other modalities can also be performed, including birefringence, luminescence (fluorescence); and diattenuation.

For direflection, the detector is arranged in reflection mode and the images measure variations in reflectivity as a function of polarisation of the sample. For diattenuation, the detector is arranged in transmission mode and the images measure variations in absorption as a function of polarisation of the sample.

For opaque materials, reflection mode is the only possibility. Examples of opaque materials which may be studied are: ceramics, geological samples (e.g. rock), metals and semiconductors. One particular application is the imaging of integrated circuit structures at various stages in the manufacturing process from semiconductor wafer to complete integrated circuit.

Biological samples, for example cells, can be imaged in transmission or reflection. Often in vivo (i.e. living) cell samples have low contrast in conventional microscopy, so polarisation contrast is useful. Polarisation contrast in live cell samples is often augmented by fluorescent tagging, for example using genetic modification with green fluorescent protein (GFP).

BRIEF DESCRIPTION OF THE DRAWINGS

This invention will now be further described, by way of example only, with reference to the accompanying drawings.

DETAILED DESCRIPTION

Figure 1:
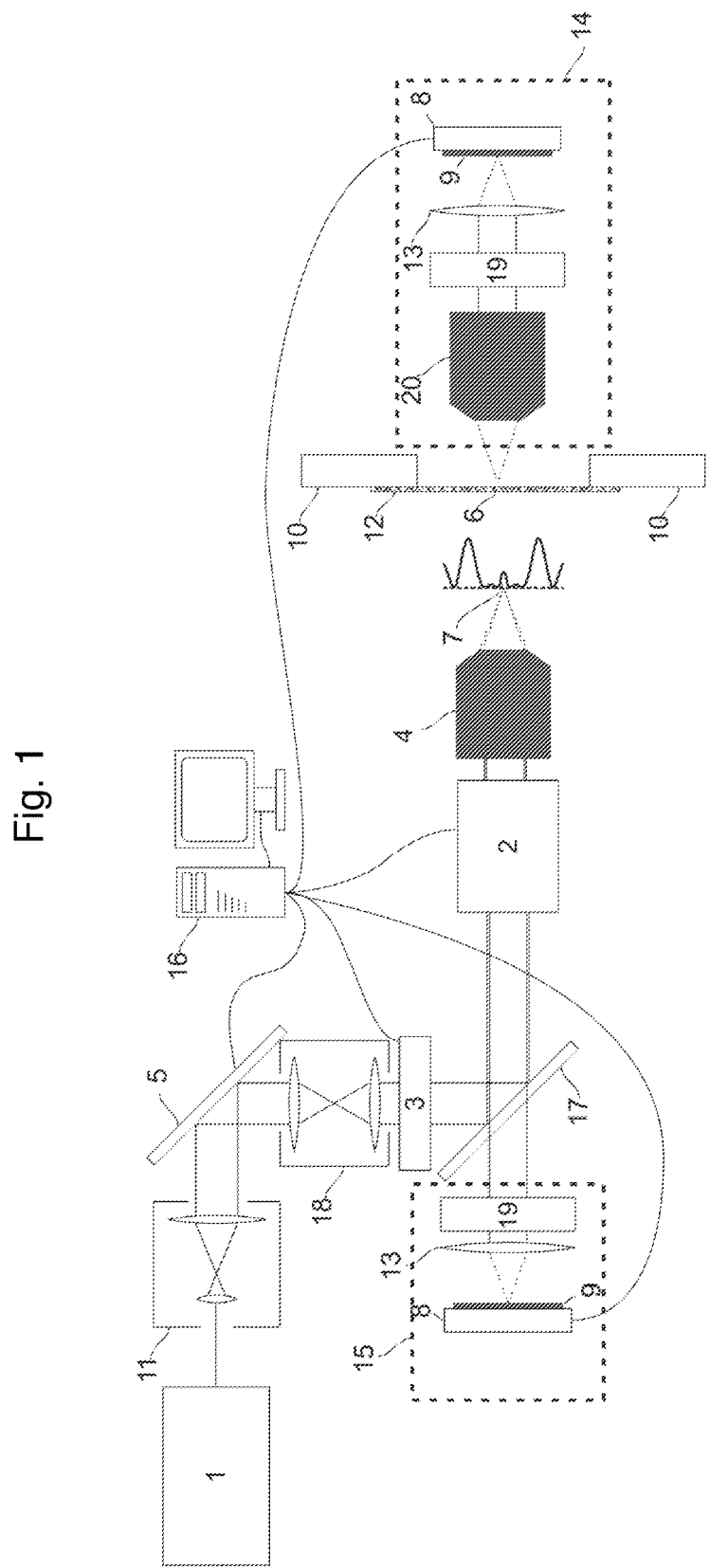
FIG. 1 shows a first embodiment.

FIG. 1 shows a first embodiment of a super-resolution polarisation microscope for imaging a sample 6.

A light source in the form of a laser 1 emits a monochromatic beam which is expanded by a beam expander 11. It will be understood that the light beam needs to have a defined polarisation, which will generally be the case for a laser emission. Other high brightness, constant intensity, monochromatic light sources could be used, such as conventional lamps (halogen, arc) or light emitting diodes (LEDs). The light source can be used in combination with any necessary or desired bandpass filters, polarisation scramblers, power stabilisers, spatial filters or other standard optical elements. It is noted that, depending on the light source's characteristics, a beam expander may not be necessary.

The light beam is then shaped in amplitude and/or phase by a spatial light modulator 5 which may be a programmable (i.e. reconfigurable) LCD panel, or some sort of fixed (i.e. not reconfigurable) mask. The spatial light modulator may be a reflective device (as shown) or a transmissive device. It is known that programmable spatial light modulators may be configured to provide super-resolution lensing as described, for example, in Baumgartl et al, Applied Physics Letters 98, 181109 (2011) [ref. 5], Mazilu et al, Opt. Exp., 19(2) 933 (2011) [ref. 6] and in U.S. Pat. No. 9,007,451 [ref. 7], with the embodiment of FIG. 9 therein, the relevant portions of which are incorporated by reference. Other known design approaches for the mask are also possible.

The shaped beam is relayed by a telescope 18 through a polarisation controller 3 which can be a conventional "PolScope" component as commercially available as the OpenPolScope hardware kit from the OpenPolScope Resource at MBL, among others, and as described in Oldenbourg [ref. 3], where it is called a "Universal Compensator". The shaped and polarised beam is then reflected from a beam splitter 17, which may optionally be dichroic, into a beam scanner 2. The beam scanner 2 could be of the galvanometer type—either resonant or non-resonant. After the beam scanner, the light beam passes through a focusing objective lens 4. The focusing objective 4 focuses the light beam to a sub-diffraction-limited spot with sidebands as schematically illustrated with an intensity profile centred about the principal optical axis. The focal plane is indicated by the dashed line. The intensity profile in the focal plane can be seen to have a relatively low intensity peak at the focus—the "spot"—as well as a number of sideband peaks. As schematically illustrated by the intensity distribution profile around the optical axis, the sidebands can contain more power than the central focus, there being a trade off between the size of the central focus 6 and its intensity. However, since the central focal spot is separated from the sidebands by a relatively dark annular region, unwanted signal arising from scattering by the sample from light in the sidebands can be rejected from the detector using a confocal approach. By sub-diffraction-limit, we mean that the intensity profile of the central focal spot in the focal plane has a full width half maximum of less than half the wavelength.

The sample 6 is held on a sample stage 10 with a sample support 12 to position the sample 6 in the focal plane. To build up an image, the small spot is scanned across the sample 6 using the beam scanner 2.

After being incident on the sample, the light beam can be collected in transmission or reflection (sometimes called 'epi'). FIG. 1 illustrates collection optics arrangements for both transmission mode and reflection mode with respective reference numerals 14 and 15. One or both may be provided in any given system.

The reflection mode components 15 include components shared with the illumination, namely the objective lens 4, scanning system 2 and beam splitter 17 as well as a polarisation analyser 19 in the form of a circular polariser, a tube lens 13, a pin hole 9 and a detector 8. Equivalently, a camera could be used with an "electronic" pinhole.

At each point of illumination on the sample, as the spot is scanned across the sample, the detector records the intensity of the light incident on the detector, building up an image pixel by pixel. The image corresponds to the intensity of the light transmitted or reflected by the sample at a particular position and for specific polarisation controller settings and modulator settings. Here we note that reference to pixels does not imply that we mean the actual physical pixels of an array detector, but rather a pixel of any desired size in a digital image being acquired. Pixel is thus a reference to an area in the focal plane centred on a particular xy-coordinate which will provide a pixel in the acquired image.

The transmission mode components 14 are more or less the same as those of the detection system as the reflection mode, but placed behind the sample. However, in this case, an additional imaging objective 20 is required and the beam splitter 17 is not required.

In transmission mode configurations of the microscope, an imaging objective is provided for collection of the light from the sample. The imaging objective may be supplemented by one or more further lensing elements and other optical elements for suitably directing the light onto the detector.

In reflection mode configurations of the microscope, the focusing objective also functions as the imaging objective usually in combination with other lens elements positioned towards the detector in a portion of the beam after a beam splitter has separated out the light for collection from the common illumination-and-collection portion of the beam path.

The detector 8, either physically or electronically, selects only that light that comes from the central focal spot (or more precisely only from where the central focal spot would be in the absence of the sample), and thus discards (i.e. rejects) the light that is scattered by the sample from the sidebands. To build up an image of the sample, the spot is scanned relative to the sample and, for each position, the total light transmitted from the central spot is recorded, in a manner similar to that used in confocal microscopy. This builds up an image of the sample, pixel by pixel. It is noted that the focus on the sample is conjugate to the focus on the detector.

The detector 8 may be a single channel (or point) detector such as a p-i-n diode, an avalanche photodiode or photomultiplier tube (PMT), or it may be an array (i.e. pixelated) detector such as a CCD or CMOS camera.

The mention above to the detector physically or electronically selecting the light component of interest refers to use of an array detector as a combined detector and pin hole, in that only detector pixels centred around a "virtual" or "electronic" pin hole location need be recorded, so that a physical pin hole can be omitted.

It will be understood that relevant components are under computer control from a computer 16 with appropriate communication lines as schematically indicated, including at least the programmable spatial light modulator 5 (to configure it for beam shaping), the polarisation controller 3 (to control the retardances of its light retarders), the beam scanner 2, and the detector 8. Moreover a suitable display device and recording device are also provided as would be incorporated in the schematically illustrated personal computer and display, for example.

In this embodiment, or any other embodiment, the beam scanner 2 could be removed and its function taken over by lateral scanning of the sample stage 10 to scan the sample across the beam in the focal plane (xy scanning).

The relay telescope 18 is optional, but improves the relay of the designed image on the modulator 5 to the focusing objective 4. In some embodiments, the image on the modulator could be designed to take account of the propagation of light between the modulator and the objective, removing the need for the relay telescope.

The polarisation analyser 19 could be a separate element as illustrated, or, in a reflection mode configuration, its function could be incorporated into the beam splitter 17, if the beam splitter 17 is a polarising beam splitter.

Figure 2:
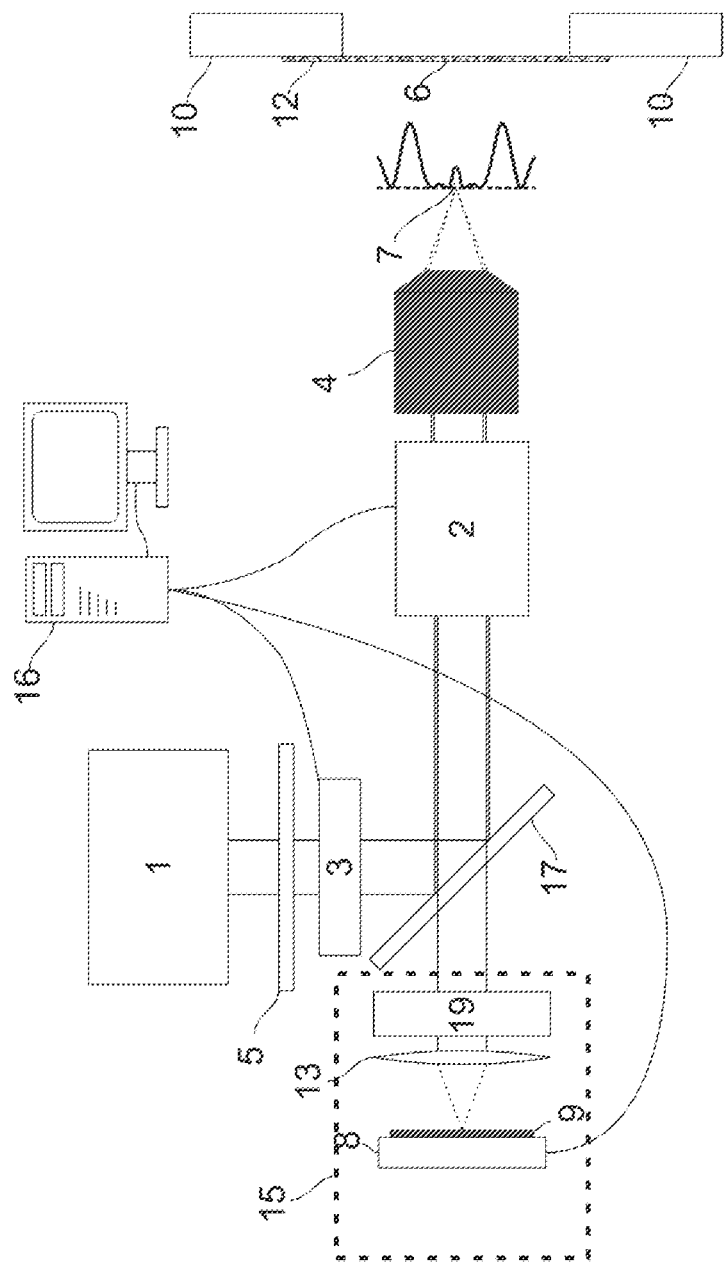
FIG. 2 shows a second embodiment.

FIG. 2 is a schematic illustration of a second embodiment which is a structurally simplified form of the first embodiment. Compared to the first embodiment, the second embodiment uses a reduced number of optical elements and has only reflection mode detection elements 15. However, the main operating principles are the same. A laser 1 generates a light beam which is passed through a transmissive mask 5, which forms a super-oscillatory lens for spatially modulating the light beam in amplitude. The light then passes through a polarisation controller 3 before being directed to a beam scanner 2 via a beam splitter 17. The light is then focused into a super-resolution spot by an objective lens 4. Light reflected or back-scattered from a sample 6 passes back through the objective lens 4, the beam scanner 2 and transmits through the beam splitter 17. The light then passes through to the detection elements 15, namely through a polarisation analyser 19 and a tube lens 13 which images the light through a pin hole 9 onto a detector 8.

Figure 3:
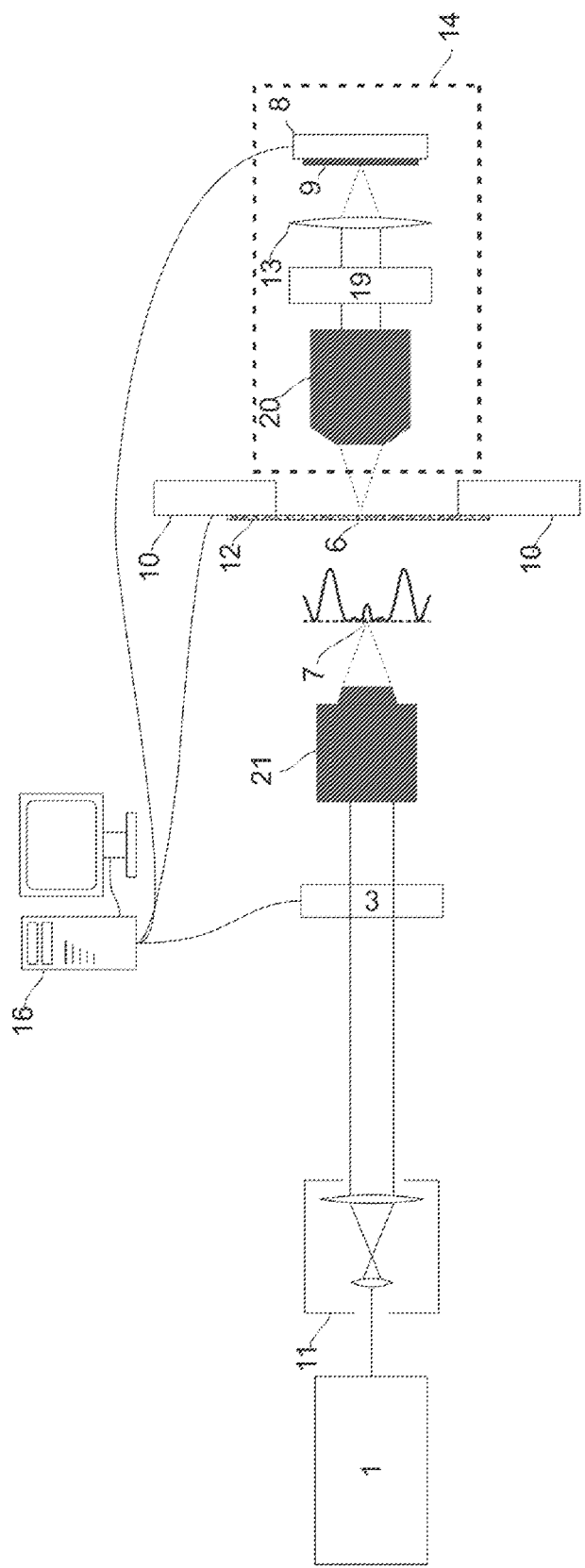
FIG. 3 shows a third embodiment.

FIG. 3 is a schematic illustration of a third embodiment using a super-oscillatory lens device as described in the embodiments of FIGS. 1 to 8 of U.S. Pat. No. 9,007,451 [ref. 7] as the spatial light modulator. The relevant portions of U.S. Pat. No. 9,007,451 describing such a lens, its design and manufacture are incorporated herein by reference. This type of super-oscillatory lens can be formed from a binary mask which is generally opaque, but is structured with a pre-defined pattern of optically transparent apertures to spatially modulate the light beam in amplitude. The binary mask is typically fabricated with an opaque material supported on a substrate of transparent material, such as a metal on silicon nitride. The substrate may be thinned over the area of the lens so that the lens is a membrane structure. For more details we refer to U.S. Pat. No. 9,007,451 and references therein.

The microscope illustrated in FIG. 3 has a transmission mode geometry. The super-oscillatory lens 21 focuses the input beam into a sub-resolution-limit spot surrounded by sidebands, using the same interference scheme described above. By combining this lens with a polarisation controller 3 and polarisation analyser 19 in a confocal detector, a super-resolved polarisation contrast image can be obtained. In this case the system is used in transmission mode, with the same detector as in the embodiment of FIG. 1. FIG. 3 also illustrates an example where there is no beam scanning optics (Feature 2 in FIG. 1). Instead, the sample 6 is scanned relative to the beam by scanning the sample stage 10 which is provided with suitable positioners for that purpose, e.g. a pair of orthogonally arranged linear positioners for scanning in x and y respectively in the focal plane mutually orthogonal to the principal optical axis.

Comparing the embodiment of FIG. 3 with the embodiments of FIG. 1 and FIG. 2, it is noted that the relative position of the spatial light modulator 5 and the polarisation controller 5 in the beam path has been swapped. More generally, the relative order of arrangement of the spatial light modulator and polarisation controller is arbitrary, so either order can be chosen as desired based on other considerations of the particular design configuration. In FIG. 3, it is simply more convenient when using a binary mask type of super-oscillatory lens for the spatial light modulation to place the binary mask in the position where the objective would be in a conventional microscope set-up, which has the effect that the practical position for the polarisation controller is ahead of the spatial light modulator in the illumination beam path. It is further noted that in the embodiments of FIG. 1 and FIG. 2, the relative positions of the spatial light modulator and polarisation controller in the illumination beam path could be swapped.

A further set of permutations for the implementation arise when it is further noted that the polarisation controller and polarisation analyser positions before and after the sample respectively are also in principle interchangeable. All the illustrated embodiments have the polarisation controller in the illumination side and the polarisation analyser in the detection side. However, as discussed in Oldenbourg [ref. 3], these positions can be swapped.

It is further noted that in any of the above embodiments a bandpass filter may be added at the same point as the polarisation analyser 19 to image polarisation-resolved fluorescence of a sample. The light source is monochromatic in the embodiments described in detail above, but in other embodiments a light beam of multiple discrete wavelengths could be used.

Details of the imaging procedure are now described. The following imaging procedure description should be taken as being applicable to any of the above embodiments unless otherwise stated.

As is known in the art, a polarisation microscope can be used to distinguish birefringence, luminescence (i.e. fluorescence); and diattenuation. To collect a single image in any of these imaging modalities, a set of images with different retardance values are taken and then combined, i.e. a set of images is taken with different settings of the polarisation controller 3 while leaving all other settings unchanged. The number of images in the set is 4 or 5, if we follow the teaching of Oldenbourg [ref. 3]. From these images, a pixel-by-pixel calculation is carried out to determine the magnitude and orientation of the required effect at each pixel. This gives an image of the sample where the contrast mechanism is based on the response of the sample to polarised light. The polarisation control elements are designed to allow the creation of various polarisation states from linearly polarised input light. One embodiment consists of two LCD panels, each of variable retardance and oriented with their slow axes at 45° to each other.

In each of these cases, there are multiple different settings of the polarisation control elements that may be used [ref. 3]. Here we describe some possible realisations of the settings and subsequent reconstruction.

To obtain a birefringence image, the two liquid crystal panels are initially set to a retardance of $\lambda/4$ and $\lambda/2$, where $\lambda$ is the wavelength of the light to produce circularly polarised light. The polarisation analyser in this case is a circular polariser of opposite handedness to the polarisation of the light, such that for a sample with no features the transmission should be at a minimum. As the polarisation is varied the transmission should increase. Birefringence imaging would normally be used in a transmission mode of the imaging system. Then a swing value s is selected, based on the expected properties of the sample. Typical values would be in the region of 0.03 wavelengths. Four further images are taken with LC panels set to the base values plus or minus s as detailed in the table:

| Image number | LC A setting | LC B setting |
| --- | --- | --- |
| 1 | $\frac{\lambda}{4}$ | $\frac{\lambda}{2}$ |
| 2 | $\frac{\lambda}{4} + s$ | $\frac{\lambda}{2}$ |
| 3 | $\frac{\lambda}{4}$ | $\frac{\lambda}{2} + s$ |
| 4 | $\frac{\lambda}{4}$ | $\frac{\lambda}{2} - s$ |
| 5 | $\frac{\lambda}{4} - s$ | $\frac{\lambda}{2}$ |

The retardance can then be calculated following the procedure in [ref. 8]. First two intermediate terms are calculated $$\alpha = \frac{2(I_4 - I_1)}{I_1 + I_2 + I_3 + I_4 - 4I_0}$$

$$\beta = \frac{2(I_3 - I_2)}{I_1 + I_2 + I_3 + I_4 - 4I_0}$$

and these are used to calculate the retardance magnitude R and azimuth $\phi$ at each pixel independently.

$$R = \begin{cases} \frac{\lambda}{360°} \tan^{-1}\left(\sqrt{\alpha^2 + \beta^2} \tan\left(180° \frac{s}{\lambda}\right)\right) & I_1 + I_2 + I_3 + I_4 - 4I_0 \geq 0 \\ \frac{\lambda}{360°} \tan^{-1}\left(180° - \sqrt{\alpha^2 + \beta^2} \tan\left(180° \frac{s}{\lambda}\right)\right) & I_1 + I_2 + I_3 + I_4 - 4I_0 < 0 \end{cases}$$

$$\phi = \frac{1}{2} \tan^{-1}\left(\frac{\beta}{\alpha}\right)$$

noting that the signs of a and b must be considered to place the angle in the correct quadrant. The accuracy of the calculations can be improved using a background correction procedure as detailed in another publication by the Oldenbourg group [ref. 8].

While birefringence imaging has proved a powerful tool for unlabelled biological imaging, and can be used with the microscopes described herein, it could be advantageous to have a technology compatible with standard laser scanning confocal geometries, while still allowing unlabelled polarisation-contrast imaging.

In embodiments of the present invention, this is possible by measuring in reflection mode the variations in reflectivity as a function of polarisation of structured materials. We believe this modality is novel and call it "direflection", in analogy to the known transmission mode modality of diattenuation.

To obtain a direflection image, a polarisation analyser may be omitted. The liquid crystal panels of the polarisation controller are set to produce linearly polarised light of various angles θ using settings on LC A of λ/4 and LC B of θλ/π. If the panels are set to 4 settings rotated by 45° with respect to each other (0°, 45°, 90°, 135°) to obtain images with intensity $I_0$, $I_{45}$, $I_{90}$, $I_{135}$ then we obtain the direflection by first calculating intermediate results $$\alpha = I_0 - I_{90}$$

$$\beta = I_{45} - I_{135}$$

$$\gamma = I_0 + I_{45} + I_{90} + I_{135}$$

and then calculating the azimuth $\phi$ and magnitude of diattenuation d as $$\phi = \frac{1}{2}\tan^{-1}\left(\frac{\beta}{\alpha}\right)$$

$$d = \frac{2\sqrt{\alpha^2 + \beta^2}}{\gamma}$$

A similar process may be followed in a transmission mode to obtain a diattenuation image, where the absorption of the object depending on the differences in absorption for different polarisations.

In summary, different embodiments of a super-resolution scanning confocal polarisation contrast microscope have been described. The microscope has a laser light source 1, sample stage 10 for mounting a sample 6 and detector 8. A polarisation controller 3 is used to set the polarisation state of the light beam to any one of a defined set of different polarisation states. A spatial light modulator 5 modulates the light beam in amplitude and/or phase to focus a sub-diffraction-limit central spot on the sample together with unwanted sidebands. A scanning confocal scheme is used in which an imaging lens 4, 20 is arranged to relay light from the sample to the detector 8 such that the focus on the detector is conjugate to that on the sample. A pin hole 9 is arranged in front of the detector 8 so that only that portion of the light is detected which has comes from the central spot, while rejecting light that has been scattered by the sample from the sidebands. Polarisation contrast images with sub-diffraction limit resolution can thus be acquired.

REFERENCES

1. U.S. Pat. No. 5,521,705
2. U.S. Pat. No. 7,202,950
3. Oldenbourg, November 2003, "Polarization microscopy with the LC-PolScope" and also an abridged version of this article in: R. D. Goldman and D. L. Spector, editors. Live Cell Imaging: A Laboratory Manual. Cold Spring Harbor, N.Y.: Cold Spring Harbor Laboratory Press. p 205-37 (2005).
4. U.S. Pat. No. 6,856,391
5. Baumgartl et al, Applied Physics Letters 98, 181109 (2011)
6. Mazilu et al. 2011 [10] Opt. Exp., 19(2) 933 (2011)
7. U.S. Pat. No. 9,007,451
8. S. B. Mehta, M. Shribak, and R. Oldenbourg, J. Opt. 15, 094007 (2013)
9. McKenna, C., Walsh, K., Crain, M., & Lake, J. (2010). Maskless direct write grayscale lithography for MEMS applications. Biennial University/Government/Industry Microelectronics Symposium—Proceedings. http://doi.org/10.1109/UGIM.2010.5508906
10. Waits, C. M., Morgan, B., Kastantin, M., & Ghodssi, R. (2005). Microfabrication of 3D silicon MEMS structures using gray-scale lithography and deep reactive ion etching. Sensors and Actuators, A: Physical, 119(1), 245-253. http://doi.org/10.1016/j.sna.2004.03.024
11. Wang, Q., Maddock, J., Rogers, E. T. F., Roy, T., Craig, C., Macdonald, K. F., Zheludev, N. I. (2014). 1.7 Gbit/in.2 gray-scale continuous-phase-change femtosecond image storage. Applied Physics Letters, 104(12), 121105. http://doi.org/10.1063/1.4869575

The invention claimed is:

1. A microscope comprising:
   a light source operable to generate a light beam of a particular wavelength;
   a sample stage configured to position a relevant portion of a sample in a sample position at a focus of the light beam;
   a detector arranged to collect light from the sample position to collect a sample image for display;
   a polarisation controller arranged in the light beam either before or after the sample position and operable to set the polarisation state of the light beam to any one of a defined set of different polarisation states;
   a spatial light modulator arranged to receive the light beam from the light source before the sample position, the spatial light modulator being configured to spatially modulate the light beam in amplitude and/or phase so that it focuses the light beam at the sample position in a focal plane with an intensity profile having a central peak with a full width half maximum of less than half the wavelength and sideband peaks; and
   a pin hole arranged to permit only that portion of the light beam to be detected by the detector which has comes from the central peak, while rejecting portions of the light beam that have been scattered by the sample from the sideband peaks.

2. The microscope of claim 1, wherein the polarisation controller comprises first and second variable light retarders each of which is independently controlled to set the polarisation state to one of the defined set of different polarisation states.

3. The microscope of claim 1, wherein the spatial light modulator is configurable under computer control to provide at least one defined spatial modulation of the light beam in amplitude and/or phase.

4. The microscope of claim 1, wherein the spatial light modulator comprises a fixed mask structured to spatially modulate the light beam in amplitude and/or phase.

5. The microscope of claim 4, wherein the fixed mask is a binary mask configured to spatially modulate the light beam in amplitude.

6. The microscope of claim 4, wherein the fixed mask is a variable amplitude and phase mask configured to spatially modulate the light beam in amplitude and phase.

7. The microscope of claim 1, further comprising a beam scanner arranged before the sample position to scan the light beam laterally over the sample position.

8. The microscope of claim 1, wherein the sample stage is provided with position elements to scan the sample position laterally across the light beam.

9. The microscope of claim 1, wherein the polarisation controller is arranged in the light beam either before or after the sample position in combination with a polarisation analyser arranged respectively after or before the sample position.

10. The microscope of claim 1, wherein the detector and pin hole are arranged to collect light transmitted through the sample position in transmission mode.

11. The microscope of claim 1, wherein the detector and pin hole are arranged to collect light reflected from the sample position in reflection mode.

12. A confocal imaging method comprising:
(a) providing an object to be imaged;
(b) generating a light beam of a particular wavelength;
(c) configuring a polarisation controller to retard the light beam before or after the sample by an amount which sets the polarisation state of the light beam to one of a defined set of different polarisation states;
(d) spatially modulating the light beam in amplitude and/or phase to create a focused spot at the sample having an intensity profile in the focal plane with a full width half maximum of less than half the wavelength;
(e) traversing the focused spot across an area of the sample and for each spot position on the sample measuring the light intensity distribution across a conjugate image plane where a detector is positioned in order to build up an image specific to the current polarisation state;
(f) repeating the steps (c), (d) and (e) for each of the other polarisation states to collect corresponding images and thereby completely to acquire said set of images; and
(g) combining said set of images into a single polarisation contrast image.

13. The method of claim 12, further comprising storing the polarisation contrast image.

14. The method of claim 12, further comprising displaying the polarisation contrast image using a display device.

15. The method of claim 12, wherein the detector is arranged in reflection mode and the images measure variations in reflectivity as a function of polarisation of the sample.

16. The method of claim 12, wherein the detector is arranged in transmission mode and the images measure variations in absorption as a function of polarisation of the sample.

* * * * *